United States Patent
Pan et al.

(10) Patent No.: US 10,738,058 B2
(45) Date of Patent: Aug. 11, 2020

(54) METHOD OF MANUFACTURING 4-CHLORO-7H-PYRROLO[2,3-D]PYRIMIDINE

(71) Applicant: Siegfried (Nantong) Pharmaceuticals Co. Ltd., Nantong Jiangsu (CN)

(72) Inventors: Ben Pan, Nantong (CN); Jiang Chen, Haimen (CN); Bernhard Berger, Konolfingen (CH); Beat Weber, Zofingen (CH)

(73) Assignee: Siegfried (Nantong) Pharmaceuticals Co. Ltd., Nantong Jiangsu (CN)

( * ) Notice: Subject to any disclaimer, the term of this patent is extended or adjusted under 35 U.S.C. 154(b) by 0 days.

(21) Appl. No.: 16/324,475

(22) PCT Filed: Aug. 11, 2017

(86) PCT No.: PCT/IB2017/054902
§ 371 (c)(1),
(2) Date: Feb. 8, 2019

(87) PCT Pub. No.: WO2018/029641
PCT Pub. Date: Feb. 15, 2018

(65) Prior Publication Data
US 2019/0169200 A1     Jun. 6, 2019

(30) Foreign Application Priority Data
Aug. 11, 2016   (CN) .................. 2016 1 06558063

(51) Int. Cl.
C07D 487/04     (2006.01)
B01D 9/00       (2006.01)

(52) U.S. Cl.
CPC ............ C07D 487/04 (2013.01); B01D 9/005 (2013.01)

(58) Field of Classification Search
None
See application file for complete search history.

(56) References Cited

U.S. PATENT DOCUMENTS

| | | | |
|---|---|---|---|
| 8,410,265 B2 | 4/2013 | Zhou et al. | |
| 2005/0222254 A1 | 10/2005 | Brodney et al. | |
| 2006/0183761 A1 | 8/2006 | Ledeboer et al. | |
| 2007/0004762 A9 | 1/2007 | Ledeboer et al. | |
| 2011/0118248 A1 | 5/2011 | Ungashe et al. | |
| 2013/0053341 A1 | 2/2013 | Suzuki et al. | |

FOREIGN PATENT DOCUMENTS

| | | | |
|---|---|---|---|
| CN | 104860950 | 8/2015 | |
| CN | 105622616 A | 6/2016 | |
| CN | 105732637 | 7/2016 | |
| CN | 106397443 | 2/2017 | |
| JP | 6121658 | 4/2017 | |
| WO | WO-2010083283 A2 * | 7/2010 | ........... C07D 487/04 |

OTHER PUBLICATIONS

Extended European Search Report corresponding to European Patent Application No. 17838907.8 dated Oct. 15, 2019.
Office Action corresponding with Chinese Patent Application No. 2016106558063 dated Jul. 5, 2019.
International Preliminary Report on Patentability for PCT/IB2017/054902 dated Feb. 12, 2019.
International Search Report on Patentability for PCT/IB2017/054902 dated Feb. 15, 2018.
Written Opinion ofthe International Search Authority for PCT/IB2017/054902 dated Feb. 15, 2018.

* cited by examiner

*Primary Examiner* — Susanna Moore
(74) *Attorney, Agent, or Firm* — Jenkins, Wilson, Taylor & Hunt, P.A.

(57) ABSTRACT

The present invention discloses a method of manufacturing 4-chloro-7H-pyrrolo[2,3-d]pyrimidine comprising the steps: a) Preparing ethyl 2-cyano-4,4-dimethoxybutanoate by coupling ethyl 2-cyanoacetate and 2-bromo-1,1-dimethoxyethane; b) Preparing 6-amino-5-(2,2-dimethoxyethyl)pyrimidin-4-ol by adding formamidine to ethyl 2-cyano-4,4-dimethoxybutanoate; c) Converting 6-amino-5-(2,2-dimethoxyethyl)pyrimidin-4-ol to 7H-pyrrolo[2,3-d]pyrimidin-4-ol; and d) Converting the 7H-pyrrolo[2,3-d]pyrimidin-4-ol to 4-chloro-7H-pyrrolo[2,3-d]pyrimidine. The method offers increased yield, less by-products and a decrease in waste compared to methods known as being state of the art.

14 Claims, No Drawings

METHOD OF MANUFACTURING 4-CHLORO-7H-PYRROLO[2,3-D]PYRIMIDINE

FIELD OF THE INVENTION

The present invention relates to a novel method of manufacturing 4-chloro-7H-pyrrolo[2,3-d]-pyrimidine. The method is characterized in that higher yield, less by-products and a decrease in waste offers ecological and economical advantages compared to methods already known and used as being state of the art. Title compound 4-chloro-7H-pyrrolo[2,3-d]pyrimidine is one key intermediate to prepare various substances.

STATE OF THE ART 4-chloro-7H-pyrrolo[2,3-d]pyrimidine is a key intermediate when preparing active pharmaceutical ingredients. The substance is known in the literature as being an intermediate to manufacture including but not limited to ruxolitinib, tofacitinib, oclacitinib, baricitinib, itacitinib, AZD-5363 and pevonedistat for example.

WO 2010/083283 discloses some steps of the presented invention. The presented synthesis has long reaction times and leads to low yields. The method for preparing ethyl 2-cyano-4,4-diethoxybutanoate (2-cyano-4,4-diethoxy-butyric acid ethyl ester) starting with bromoacet-aldehyde diethylacetal has a theoretical yield of 57%. The preparation of 7H-pyrrolo[2,3-d]-pyrimidin-4-ol has a theoretical yield of 68.3%. The preparation of 4-chloro-7H-pyrrolo[2,3-d]pyrimidine from of 7H-pyrrolo[2,3-d]pyrimidin-4-ol had an yield of 67.8% using sodium hydroxide (20%).

CN 102526087 discloses a synthesis which uses thio urea, a strong acid and Raney nickel to prepare 4-chloro-7H-pyrrolo[2,3-d]pyrimidine from ethyl 2-cyano-4,4-diethoxybutanoate.

State of the art and importance of the molecule show the need of presenting a novel method having good yield, working in well controllable and safe range, leading to improved purity and decreasing the amount of waste while offering a way of recycling not reacted material and solvents.

SUMMARY OF THE INVENTION

The current invention offers a novel method for manufacturing 4-chloro-7H-pyrrolo[2,3-d]-pyrimidine in a reaction sequence having 4 steps only, high yield, high purity and also offering a safe, economic and ecologic process.

The present invention relates to a method for preparing 4-chloro-7H-pyrrolo[2,3-d]pyrimidine:

following the reaction as disclosed in the following scheme 1:

Scheme 1

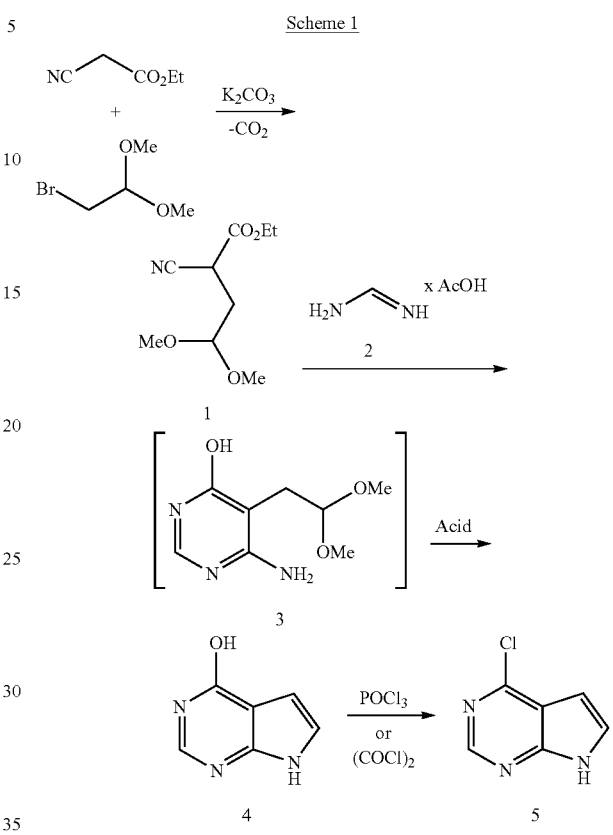

Inventors found different measures and conditions to have a short route of synthesis by using well controllable synthetic steps, also reducing waste by using less solvents, showing an easy way of recovering starting material and solvents. In one aspect of the invention the overall yield has been increased. In one aspect of the invention purity of the end product is such that no additional purification step is required for further processing the end product.

DETAILED DESCRIPTION OF THE PRESENT INVENTION

All ranges disclosed herein are to be considered to be supplemented by the term "about", unless clearly defined to the contrary or otherwise clear from the context.

The current invention offers a novel method for manufacturing 4-chloro-7H-pyrrolo[2,3-d]-pyrimidine in a reaction having 4 steps only as disclosed in detail below.

In one aspect of the invention the process offers the manufactured end product 4-chloro-7H-pyrrolo[2,3-d]pyrimidin in purity of more than 99.5 area-% measured by HPLC without applying any further purification step. In various trials purity levels of 99.5 area-%, 99.7 area-%, 99.8 area-% or equal to or above 99.9 area-% have been observed.

In one aspect of the invention the first step of the reaction is performed with an excess of ethyl 2-cyanoacetate of 1.5 up to 10 times the molar ration 2-bromo-1,1-dimethoxy-ethane. Inventors found the reaction to give high conversion rates in this particular step conversion rates of 75% or more than 75%, i.e. 75% to 80% whereas expectations from literature are below 60%. Also yields of 80%, or of 80% to 85% have been reached. The ethyl 2-cyanoacetate that was added in excess and that did not react can easily be recovered together with the solvent by distillation and to be used without loss for the next production batch.

In one aspect of the invention the addition of the carbonate salt in step 1 is not only done slowly but also the amount is divided into three or more discrete portions. The individual portions are added such that the released carbon dioxide can exhaust in a safely and well controllable manner. It is even desirable to dose a portion after development of carbonate gas from the previous portion has ceased. An increase in yield and in purity have been observed.

In one aspect of the invention it has been observed that even educts being of medium quality will result in an intermediate having high purity and high yield.

In one aspect of the invention it has been observed that when using potassium hydroxide to adjust the pH value into the desired range of 8.0 or above, preferably of 8.0 to 9.0, for the conversion of 7H-pyrrolo[2,3-d]pyrimidin-4-ol to 4-chloro-7H-pyrrolo[2,3-d]-pyrimidine the yield had increased by at least 5% compared to examples in which other hydroxide salts have been used. In a different embodiment an increase of 10%, in further embodiments an increase of equal or more than 15% has been found.

In one aspect of the invention the product manufactured following the novel process can be converted into other chemical substances that are used as intermediate in many technical, pharmaceutical or other application. Especially the conversion to 7-tosyl derivative (4-chloro-7-tosyl-7H-pyrrolo[2,3-d]pyrimidine) offers various options.

In one aspect of the inventions it has been found to be advantageous to precipitate title compound from a mixture of an organic solvent and water, more specifically it has been found it is advantageous using a mixture of toluene and water.

EXAMPLES

The present invention will now be described in detail with reference to several examples thereof. However, these examples are illustrative and do not limit the scope of the invention.

Example 1

Ethyl 2-cyano-4,4-dimethoxybutanoate (1)

A mixture of 421 g (3.73 mol) ethyl 2-cyanoacetate, 150 g (0.89 mol) 2-bromo-1,1-dimethoxyethane (molar ratio: 4.2:1.0), 30 g potassium carbonate and 7.0 g potassium iodide is heated to 130° C. 92 g potassium carbonate are added in not less than 3 portions at such a slow rate that the off gas stream is vented safely (1.5 hours, typically 1 to 2 hours). The mixture is kept at reflux (about 120° C.) until the reaction is complete. The reaction mixture is cooled and the inorganic substances are dissolved in 375 g of water. Phases are separated and the organic phase is washed with zoo g water. The aqueous phases are combined and extracted with 300 g toluene. The organic phases are combined and distilled under vacuum. Toluene and excess of ethyl 2-cyanoacetate are recovered for next batches. 146 g of product (yield: 0.73 mol, 82% conversion rate) are isolated at about 110° C. (<1 mbar) having a purity of 90 area-% measured by HPLC.

Comparative Example 1a

A mixture of 113 g (to mol) ethyl 2-cyanoacetate, 150 g (0.89 mol) 2-bromo-1,1-dimethoxyethane (molar ratio: 1.12:1.0), 30 g potassium carbonate and 7.0 g potassium iodide is heated to 130° C. 92 g potassium carbonate are added in not less than 3 portions at such a slow rate that the off gas stream is vented safely (1 to 2 hours). The mixture is kept at reflux (about 120° C.) until the reaction is complete. The reaction mixture is cooled and the inorganic substances are dissolved in 375 g of water. Phases are separated and the organic phase is washed with zoo g water. The aqueous phases are combined and extracted with 300 g toluene. The organic phases are combined and distilled under vacuum. 87 g of product (yield: 0.43 mol, 49% conversion rate) are isolated at about 110° C. (<1 mbar) having a purity of 85 area-% measured by HPLC.

Comparative Example 1b

A mixture of 421 g (3.73 mol) ethyl 2-cyanoacetate, 150 g (0.89 mol) 2-bromo-1,1-dimethoxyethane (molar ratio: 4.2:1.0), 30 g potassium carbonate and 7.0 g potassium iodide is heated to 130° C. 92 g potassium carbonate are added slowly during 5 minutes. The mixture is kept at reflux (about 120° C.) until the reaction is complete. The reaction mixture is cooled and the inorganic substances are dissolved in 375 g of water. Phases are separated and the organic phase is washed with 200 g water. The aqueous phases are combined and extracted with 300 g toluene. The organic phases are combined and distilled under vacuum. 133 g of product (yield: 0.67 mol, 74% conversion rate) are isolated at about 110° C. (<1 mbar) having a purity of 83 area-% measured by HPLC.

Comparative Example 1c

A mixture of 113 g (1.0 mol) ethyl 2-cyanoacetate, 150 g (0.89 mol) 2-bromo-1,1-dimethoxyethane (molar ratio: 1.12:1.0), 30 g potassium carbonate and 7.0 g potassium iodide is heated to 130° C. 92 g potassium carbonate are added slowly during 5 minutes. The mixture is kept at reflux (about 120° C.) until the reaction is complete. The reaction mixture is cooled and the inorganic substances are dissolved in 375 g of water. Phases are separated and the organic phase is washed with 200 g water. The aqueous phases are combined and extracted with 300 g toluene. The organic phases are combined and distilled under vacuum. 80 g of product (yield: 0.40 mol, 45% conversion rate) are isolated at about 110° C. (<1 mbar) having a purity of 79 area-% measured by HPLC.

Example 2

7H-pyrrolo[2,3-d]pyrimidin-4-ol (4)

To a mixture of 95.5 g (0.92 mol) formamidine acetate and 600 g sodium ethoxide (20% by weight in ethanol) are added 126 g (0.63 mol) ethyl 2-cyano-4,4-dimethoxybutanoate (technical grade: 90 weight-% purity). The reaction mixture is refluxed until reaction is complete. The batch is slightly cooled and filtered. The filtrate is concentrated in vacuum and the residue is diluted with 74 g water. Distillation is continued and the batch is supplemented with 632 g water. The reaction mixture containing 6-amino-5-(2,2-dimethoxyethyl)pyrimidin-4-ol (3) is directly processed further. The reaction mixture is acidified by adding 185 g hydrochloric acid (aqueous solution, 32 weight-%). The batch is aged at 45° C. until cyclization is complete, then cooled to room temperature and pH is adjusted to 4 (target pH range is 3 to 5) by addition of concentrated sodium hydroxide solution. The product is isolated, washed with water and dried under vacuum at not more than 100° C. yielding 64 g (yield: 0.47 mol, 75% conversion rate) of the title compound with 99.8 area-% purity measured by HPLC.

Example 3

7H-pyrrolo[2,3-d]pyrimidin-4-ol (4)

To a mixture of 95.5 g (0.92 mol) formamidine acetate and 600 g sodium ethoxide (20% by weight in ethanol) are added 126 g (0.63 mol) ethyl 2-cyano-4,4-dimethoxybutanoate (technical grade: 80 weight-% purity). The reaction mixture is refluxed until reaction is complete. The batch is concentrated in vacuum and the residue is diluted with 74 g water. Distillation is continued and the batch is supplemented with 632 g water. The reaction mixture containing 6-amino-5-(2,2-dimethoxyethyl)pyrimidin-4-ol (3) is directly processed further. The reaction mixture is acidified by adding 226 g hydrochloric acid (aqueous solution, 32 weight-%). The batch is aged at 45° C. until cyclization is complete, then cooled to room temperature and pH is adjusted to 4 (target pH range is 3 to 5) by addition of concentrated sodium hydroxide solution. The product is isolated, washed with water and dried under vacuum at not more than 100° C. yielding 55 g (yield: 0.41 mol, 65% conversion rate) of the title compound with 99.8 area-% purity measured by HPLC.

Example 4

4-chloro-7H-pyrrolo[2,3-d]pyrimidine (5)

A mixture of 86 g (0.64 mol) 7H-pyrrolo[2,3-d]pyrimidin-4-ol, 185 g phosphoryl chloride and 373 g toluene are warmed to 50° C. 97 g of N,N-diisopropylethylamine are added in portions. Temperature is kept at 50° C. until reaction is complete. The batch is poured onto 770 g water at a maximal temperature of 35° C., made alkaline (pH 8-9) by addition of concentrated potassium hydroxide solution and is aged at a temperature below 35° C. for a minimum of 1 hour. The product is then centrifuged, washed with water and dried under vacuum at a temperature below 80° C., yielding 82 g (yield: 0.54 mol, 84% conversion rate) of 4-chloro-7H-pyrrolo[2,3-d]pyrimidine having a purity of 99.9 area-%, measured by HPLC.

Comparative Example 4a 4-chloro-7H-pyrrolo[2,3-d]pyrimidine (5)

A mixture of 86 g (0.64 mol) 7H-pyrrolo[2,3-d]pyrimidin-4-ol, 185 g phosphoryl chloride and 373 g toluene are warmed to 50° C. 97 g of N,N-diisopropylethylamine are added in portions. Temperature is kept at 50° C. until reaction is complete. The batch is poured onto 770 g water at a maximal temperature of 35° C., made alkaline (pH 8-9) by addition of concentrated sodium hydroxide solution and is aged at a temperature of 40° C. for a minimum of 1 hour. The product is then centrifuged, washed with water and dried under vacuum at a temperature below 80° C., yielding 77 g (yield: 0.51 mol, 79% conversion rate) of 4-chloro-7H-pyrrolo[2,3-d]pyrimidine having a purity of 99.8 area-% measured by HPLC.

Example 5

4-chloro-7-tosyl-7H-pyrrolo[2,3-d]pyrimidine (6)

A mixture of 66 g (0.43 mol) 4-chloro-7H-pyrrolo[2,3-d]pyrimidine, 607 g dichloromethane, 3.0 g tetrabutylammonium chloride, 90 g tosyl chloride, 85 g potassium carbonate and 381 g water is stirred efficiently at room temperature until reaction is complete. The phases are separated and the organic phase is washed with 340 g water. The organic phase is treated with 6.0 g of activated charcoal, completed with 318 g water and the organic solvent removed by distillation. The mixture is supplemented by 318 g heptane and the product is centrifuged, washed with heptane and water and vacuum dried at a temperature of not more than 80° C., yielding 124 g (yield: 0.40 mol, 94% conversion rate) of 4-chloro-7-tosyl-7H-pyrrolo[2,3-d]pyrimidine having a purity of 99.9 area-% measured by HPLC.

Description of HPLC Method

An Agilent Zorbax Eclipse Plus C18 column has been used at a flow rate of to ml/min and at a column temperature of 25° C. The gradient of the eluents water and methanol was:

| Time/min | Water/weight-% | Methanol/weight-% |
| --- | --- | --- |
| 0.0 | 5 | 95 |
| 10.0 | 95 | 5 |
| 12.0 | 95 | 5 |
| 12.1 | 5 | 95 |
| 17.0 | 5 | 95 |

The invention claimed is:

1. A method of preparing 4-chloro-7H-pyrrolo[2,3-d]pyrimidine comprising the steps:
    a) Preparing ethyl 2-cyano-4,4-dimethoxybutanoate by coupling ethyl 2-cyanoacetate and 2-bromo-1,1-dimethoxyethane;
    b) Preparing 6-amino-5-(2,2-dimethoxyethyl)pyrimidin-4-ol by adding formamidine to ethyl 2-cyano-4,4-di methoxybutanoate;
    c) Converting 6-amino-5-(2,2-dimethoxyethyl)pyrimidin-4-ol to 7H-pyrrolo[2,3-d]pyrimidin-4-ol; and
    d) Converting the 7H-pyrrolo[2,3-d]pyrimidin-4-ol to 4-chloro-7H-pyrrolo[2,3-d]pyrimidine,
    wherein the ethyl 2-cyano-acetate in step a) is added in excess to the 2-bromo-1,1-dimethoxyethane at a molar ratio of between 1.5:1.0 to 10.0:1.0, and further comprising adding carbonate in step a), wherein the carbonate is added in at least three portions.

2. The method according to claim 1, wherein the ethyl 2-cyano-acetate in step a) is added in excess to the 2-bromo-1,1-dimethoxyethane at a molar ratio between 2.0:1.0 to 4.2:1.0.

3. The method according to claim 2, wherein the excess of ethyl 2-cyano-acetate used in step a) is recycled.

4. The method according to claim 1, wherein the yield of step a) exceeds 80% of the theoretically reachable conversion rate.

5. The method according to claim 1, wherein the purity of ethyl 2-cyano-4,4-dimethoxybutanoate in step a) is above 70 area-% as measured by HPLC.

6. The method according to claim 1, wherein conditions in reaction step d) are at pH levels 8.0 or above.

7. The method according to claim 6, wherein potassium hydroxide is used to adjust the pH level in step d) to a value of 8.0 or above.

8. The method according to claim 1, wherein the product 4-chloro-7H-pyrrolo[2,3-d]pyrimidine is directly isolated from the reaction mixture by precipitation.

9. The method according to claim 1, wherein the purity of 4-chloro-7H-pyrrolo[2,3-d]pyrimidine after step d) is higher than 99.5 area-% as measured by HPLC.

10. A method for preparing 4-chloro-7-tosyl-7H-pyrrolo[2,3-d]pyrimidine, the method comprising:
  a) preparing ethyl 2-cyano-4,4-dimethoxybutanoate by coupling ethyl 2-cyanoacetate and 2-bromo-1,1-dimethoxyethane;
  b) preparing 6-amino-5-(2,2-dimethoxyethyl)pyrimidin-4-ol by adding formamidine to ethyl 2-cyano-4,4-dimethoxybutanoate;
  c) converting 6-amino-5-(2,2-dimethoxyethyl)pyrimidin-4-ol to 7H-pyrrolo[2,3-d]pyrimidin-4-ol; and
  d) converting the 7H-pyrrolo[2,3-d]pyrimidin-4-ol to 4-chloro-7H-pyrrolo[2,3-d]pyrimidine, wherein the ethyl 2-cyano-acetate in step a) is added in excess to the 2-bromo-1,1-dimethoxyethane at a molar ratio of between 1.5:1.0 to 10.0:1.0, and further comprising adding carbonate in step a), wherein the carbonate is added in at least three portions, and adding tosyl to the 4-chloro-7H-pyrrolo[2,3-d]pyrimidine to thereby prepare 4-chloro-7-tosyl-7H-pyrrolo[2,3-d]pyrimidine.

11. The method according to claim 6, wherein conditions in reaction step d) are at pH levels between 8.0 and 9.0.

12. The method according to claim 7, wherein potassium hydroxide is used to adjust the pH level in step d) to a value of between 8.0 and 9.0.

13. The method according to claim 9, wherein the purity of the 4-chloro-7H-pyrrolo[2,3-d]pyrimidine after step d) is higher than 99.7 area-% as measured by HPLC.

14. The method according to claim 9, wherein the purity of the 4-chloro-7H-pyrrolo[2,3-d]pyrimidine after step d) is higher than 99.9 area-% as measured by HPLC.

* * * * *